US00PP33152P2

(12) United States Plant Patent
de Groot

(10) Patent No.: US PP33,152 P2
(45) Date of Patent: Jun. 15, 2021

(54) ***ROSA* PLANT NAMED 'RUIRI0091A'**

(50) Latin Name: *Rosa hybrida*
Varietal Denomination: RUIRI0091A

(71) Applicant: De Ruiter Intellectual Property B.V., Amstelveen (NL)

(72) Inventor: Hendrikus Cornelis Adrianus de Groot, Amstelveen (NL)

(73) Assignee: De Ruiter Intellectual Property B.V.

( * ) Notice: Subject to any disclaimer, the term of this patent is extended or adjusted under 35 U.S.C. 154(b) by 0 days.

(21) Appl. No.: 16/987,141

(22) Filed: Aug. 6, 2020

(51) Int. Cl.
*A01H 5/02* (2018.01)
*A01H 6/74* (2018.01)

(52) U.S. Cl.
USPC ..... Plt./106
CPC ..... *A01H 6/749* (2018.05)

(58) Field of Classification Search
USPC ..... Plt./106
CPC ..... A01H 6/749
See application file for complete search history.

*Primary Examiner* — Anne Marie Grunberg
(74) *Attorney, Agent, or Firm* — Cassandra Bright

(57) ABSTRACT

A new and distinct cultivar of multiflora shrub *Rosa* plant named 'RUIRI0091A' is disclosed, characterized by large salmon/orange flowers. Foliage is dark green and very glossy. The new variety is a multiflora landscape type garden rose.

2 Drawing Sheets

Figure 1:
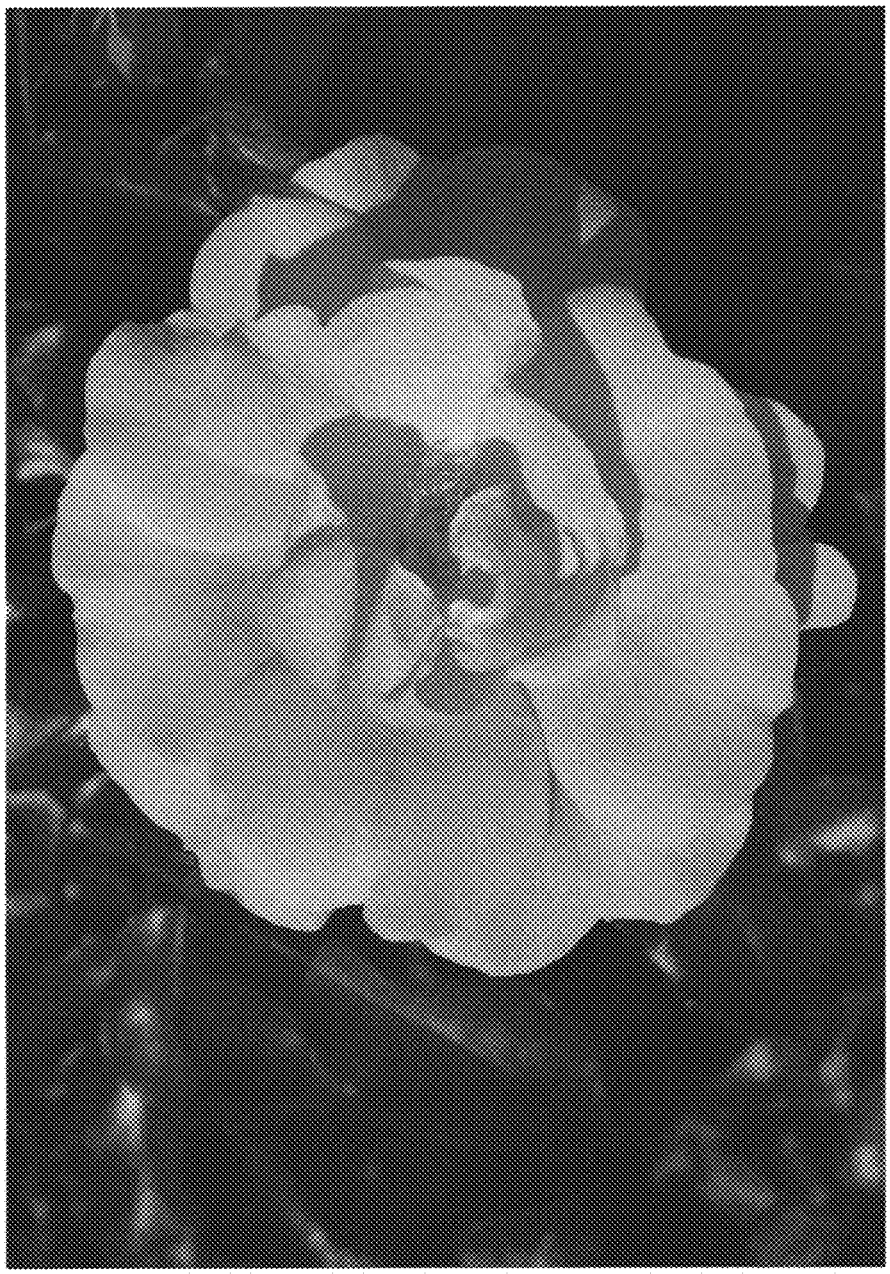

Latin name of the genus and species: *Rosa hybrida.*
Variety denomination: 'RUIRI0091A'.

BACKGROUND OF THE INVENTION

The new *Rosa* cultivar is a product of a planned breeding program conducted by the inventor. The cross resulting in this new variety was made during Spring of 2010 at a research nursery in Amstelveen, The Netherlands.

The seed parent is the unpatented variety *Rosa* 'r-02-0159-001'. The pollen parent is the unpatented variety *Rosa* 'NOA75800'. The new variety was selected in 2012 by the inventor in a group of seedlings resulting from the 2010 crossing, in a nursery in Amstelveen, the Netherlands.

Asexual reproduction of the new cultivar was performed by vegetative cuttings at a nursery in Amstelveen, The Netherlands in May 2013, and has shown that the unique features of this cultivar are stable and reproduced true to type in successive generations.

SUMMARY OF THE INVENTION

The cultivar 'RUIRI0091A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRI0091A' These characteristics in combination distinguish 'RUIRI0091A' as a new and distinct *Rosa* cultivar:

1. Orange/salmon colored flowers.
2. Glossy leaves.
3. Dark green leaf color.
4. Extremely floriferous plants.

Plants of the new cultivar 'RUIRI0091A' are similar to plants of the seed parent, in most horticultural characteristics, however, plants of the new cultivar 'RUIRI0091A' differ in the following:

1. The new variety has orange/light salmon flowers, while the seed parent has orange/pink flowers.
2. The new variety has glossier leaves than the seed parent.
3. The new variety has dark green leaves, while the seed parent has light green leaves.

Plants of the new cultivar 'RUIRI0091A' are similar to plants of the pollen parent in most horticultural characteristics, however, plants of the new cultivar 'RUIRI0091A' differs in the following;

1. The new variety has orange/light salmon flowers, while the pollen parent has orange flowers.
2. The new variety has glossier leaves than the pollen parent.
3. The new variety has dark green leaves, while the pollen parent has medium green leaves.

COMMERCIAL COMPARISON

Plants of the new cultivar 'RUIRI0091A' can be compared to the commercial variety *Rosa*, 'Harwelcome', U.S. Plant Pat. No. 9,161. These varieties are similar in most horticultural characteristics, however 'RUIRI0091A' differs in the following:

1. The new variety has a lighter petal color.
2. The new variety has less petals than this comparator.
3. The new variety is more compact than this comparator.
4. Foliage of the new variety is glossier than this comparator.

Plants of the new cultivar 'RUIRI0091A' can be compared to the commercial variety *Rosa*, 'Aprikola', unpatented. These varieties are similar in most horticultural characteristics, however 'RUIRI0091A' differs in the following:

1. The new variety has larger flowers than this comparator.

2. The new variety stronger flower stems than this comparator.

BRIEF DESCRIPTION OF THE PHOTOGRAPHS

The accompanying photograph in FIG. 1 illustrates in full color a close-up view of an individual flower.

Figure 2:
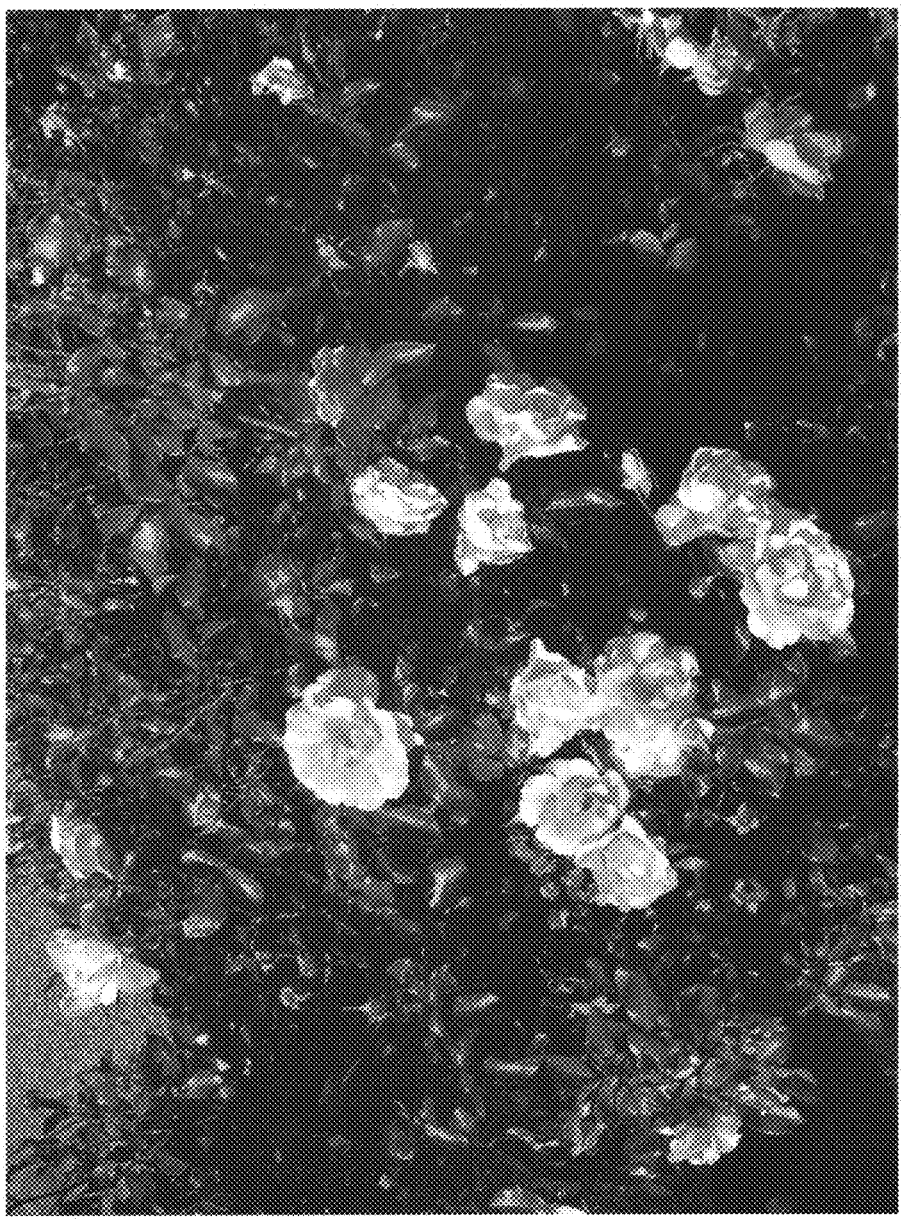

FIG. 2 illustrates a plant of the new variety grown in a trial garden at about 2 years of age.

The photographs were taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'RUIRI0091A' plants grown outdoors, in De Kwakel, The Netherlands. The growing temperature ranged from approximately 20° C. to 26° C. during the day and from approximately 16° C. to 18° C. during the night. Measurements were taken in September. General light conditions were very bright, normal sunlight. Measurements and numerical values represent averages of typical plant types.

Botanical classification: *Rosa* 'RUIRI0091A'.

*Market classification*.—Landscape/groundcover multiflora.

PROPAGATION

Time to initiate roots: About 10 days at approximately 25° C.

Time to produce a rooted cutting: About 21 days at approximately 25° C.

Typical method: Vegetative terminal cuttings, does not require grafting.

PLANT

Age of plant described: Approximately 2 years.
Growth habit: Intermediate.
Container size: Open ground.
Height: 50 cm.
Plant spread: 40 cm.
Rootstock: No graft, grown on own root.
Growth rate: Moderate.
Branching characteristics: Compound.
Length of primary lateral branches: Approximately 20 cm.
Diameter of lateral branches: Approximately 7 cm.
Quantity branches: Numerous.
Branches-young wood:
- *Diameter*.—Approximately 0.3 cm.
- *Texture*.—Smooth.
- *Approximately density/quantity of thorns*.—Very many.
- *Color*.—Near RHS Greyed-Red 178B.

Branches-old wood:
- *Diameter*.—Approximately 0.6 cm.
- *Color*.—Near RHS Yellow-Green 147C.
- *Texture*.—Smooth.

Thorns:
- *Approximately density/quantity of thorns*.—Many.
- *Color*.—Near RHS Greyed-Purple 183B.
- *Height*.—Average 0.8 cm.
- *Diameter*.—0.6 cm.

FOLIAGE

Leaf:
- *Arrangement*.—Imparipinnate.
- *Quantity*.—Average 6 per main branch.
- *Internode*.—Average 2-3 cm.
- *Average length*.—Approximately 10 cm.
- *Average width*.—Approximately 8 cm.

Leaflet:
- *Quantity*.—3, 5, or 7 per leaf.
- *Average length*.—Approximately 4.5 cm.
- *Average width*.—Approximately 2.5 cm.
- *Shape of blade*.—Ovate.
- *Apex*.—Obtuse.
- *Base*.—Obtuse.
- *Margin*.—Serrate.
- *Texture of top surface*.—Smooth.
- *Texture of bottom surface*.—Smooth.
- *Appearance*.—Very glossy upper surface, matte lower surface.
- *Color*.—Young foliage upper side: RHS Green 137B. Young foliage under side: RHS Yellow-Green 146B. Mature foliage upper side: RHS Yellow-Green 147A. Mature foliage under side: RHS Yellow-Green 147B.
- *Venation*.—Type: Pinnate. Venation color upper side: Near RHS Yellow-Green 146C. Venation color under side: Near RHS Yellow-Green 146C.

Stipule:
- *Length*.—1.3 cm.
- *Width*.—0.8 cm.
- *Color*.—RHS Green 137B.
- *Texture*.—Smooth.

Petiole:
- *Average length*.—1 cm.
- *Average diameter*.—0.2 cm.
- *Color*.—Near RHS Greyed-Greyed-Purple 183C. Base near RHS Green 137B.
- *Texture*.—Hairy.

Rachis:
- *Length*.—1.8 cm.
- *Width*.—0.2 cm.
- *Color*.—Near RHS Green 137B, flushed Greyed-Greyed-Purple 183C.
- *Texture*.—Pubescent.

FLOWER

Natural flowering season: June-October in Europe.
Begins flowering after how many years/months: 2 months.
Inflorescence type: Multiflora.
Rate of flower opening: Approximately 3 days from bud to fully opened flower.
Flower longevity on plant: 7 days, after fully opened.
Quantity of flowers: 4 flowers per multiflora.
Inflorescence size:
- *Diameter*.—Approximately 10 cm.
- *Depth*.—Approximately 8 cm.

Flower size:
- *Diameter*.—Approximately 6 cm.
- *Depth*.—Approximately 4 cm.

Peduncle:
- *Length*.—3.5 cm.
- *Diameter*.—0.2 cm.

Petals:

*Petal arrangement*.—Rotate, loose.

*Length*.—3.5 cm.

*Width*.—4 cm.

*Shape*.—Obcordate.

*Margin*.—Undulate.

*Apex*.—Retuse.

*Base*.—Obtuse.

*Petal quantity*.—15.

*Texture*.—Velvet.

*Color*.—When opening: Upper surface: Near RHS Orange 29C. Lower surface: Near RHS Red 37B. Fully opened: Upper surface: Near RHS Red 36C. Lower surface: Near RHS Red 38B.

Bud:

*Shape*.—Oval.

*Length*.—Approximately 2 cm.

*Diameter*.—Approximately 1.4 cm.

*Color*.—Near RHS Red 37B.

Sepals:

*Length*.—2.6 cm.

*Width*.—0.9 cm.

*Shape*.—Lanceolate.

*Color*.—Interior Surface: Near RHS Yellow-Green N144D. Exterior Surface: Near RHS Yellow-Green N144C.

*Texture*.—Smooth.

Receptacle:

*Length*.—0.8 cm.

*Width*.—0.7 cm.

*Shape*.—Round.

*Color*.—Near RHS Yellow-Green N144D.

Fragrance: None.

REPRODUCTIVE ORGANS

Stamens:

*Number*.—Approximately 80.

*Filament length*.—Approximately 0.7 cm.

*Filament color*.—Near RHS Yellow-Orange 16D.

Anthers:

*Length*.—3 mm.

*Shape*.—Oblong.

*Color*.—Near RHS Yellow-Orange 22A.

*Pollen*.—Color: RHS Yellow-Orange 22A. Quantity: Moderate.

Pistil:

*Number*.—Approximately 35.

*Length*.—Approximately 10 mm.

*Style*.—Length: Approximately 0.3 cm. Color: Near RHS Red 46B.

*Stigma*.—Shape: Orbicular. Color: Near RHS Greyed-Orange 168D. Ovary Color: Near RHS White NN155C.

OTHER CHARACTERISTICS

Seeds and fruits: None detected.

Disease/pest resistance: Neither resistance nor susceptibility to normal diseases and pests of Roses observed.

Temperature tolerance: USDA zones 4-9.

What is claimed is:

1. A new and distinct *Rosa* multiflora landscape type plant named 'RUIRI0091A' as herein illustrated and described.

* * * * *